(12) United States Patent
Slivka et al.

(10) Patent No.: US 7,879,102 B2
(45) Date of Patent: Feb. 1, 2011

(54) METHOD FOR TREATMENT OF DEFECTS IN THE INTERVERTEBRAL DISC

(75) Inventors: Michael Slivka, Taunton, MA (US); Hassan Serhan, South Easton, MA (US)

(73) Assignee: Depuy Acromed, Inc., Raynham, MA (US)

( * ) Notice: Subject to any disclaimer, the term of this patent is extended or adjusted under 35 U.S.C. 154(b) by 1270 days.

(21) Appl. No.: 10/676,868

(22) Filed: Sep. 30, 2003

(65) Prior Publication Data
US 2005/0069571 A1   Mar. 31, 2005

(51) Int. Cl.
*A61F 2/44* (2006.01)
(52) U.S. Cl. .................... 623/17.16; 623/902; 424/93.7
(58) Field of Classification Search ................ 424/423, 424/551; 623/17
See application file for complete search history.

(56) References Cited

U.S. PATENT DOCUMENTS

| | | | |
|---|---|---|---|
| 4,956,178 A | 9/1990 | Badylak et al. | |
| 5,281,422 A | 1/1994 | Badylak et al. | |
| 5,922,028 A | 7/1999 | Plouhar et al. | |
| 5,964,807 A | 10/1999 | Gan et al. | |
| 6,128,682 A | 10/2000 | Sharkey et al. | |
| 6,140,452 A | 10/2000 | Felt et al. | |
| 8,206,921 | 3/2001 | Guagtiano et al. | |
| 6,245,107 B1 | 6/2001 | Ferree | |
| 6,371,990 B1 | 4/2002 | Ferree | |
| 6,425,919 B1 | 7/2002 | Lambrecht | |
| 6,592,625 B2 | 7/2003 | Cauthen | |
| 6,723,335 B1 * | 4/2004 | Moehlenbruck et al. | .... 424/425 |
| 6,764,514 B1 | 7/2004 | Li et al. | |
| 2001/0023373 A1 * | 9/2001 | Plouhar et al. | ........... 623/23.72 |
| 2002/0007218 A1 | 1/2002 | Cauthen | |
| 2007/0250177 A1 * | 10/2007 | Bilbo | ....................... 623/23.72 |

FOREIGN PATENT DOCUMENTS

| | | |
|---|---|---|
| WO | WO 99/04720 A1 | 2/1999 |
| WO | WO 99/61084 A1 | 12/1999 |
| WO | WO 00/62832 A1 | 10/2000 |
| WO | WO 01/10316 A1 | 2/2001 |
| WO | WO 01/12107 A1 | 2/2001 |
| WO | WO 02/45765 A2 | 6/2002 |
| WO | WO 03/051239 A1 | 6/2003 |

* cited by examiner

*Primary Examiner*—Allison M Ford

(57) ABSTRACT

A minimally invasive spinal disc defect repair method is disclosed. The method relates to insertion of disc defect repair materials that are substantially two-dimensionally shaped and which allow for insertion and preferably self retention within the disc defect with plugging of the annulus fibrosis.

19 Claims, 2 Drawing Sheets

FIG. 1
FIG. 2
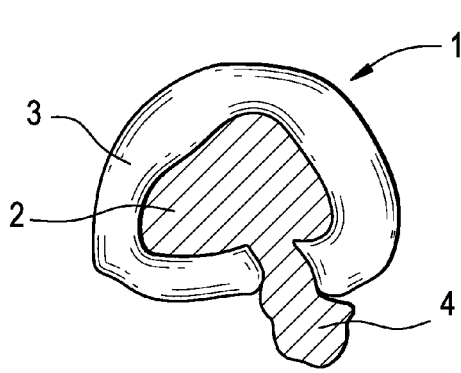
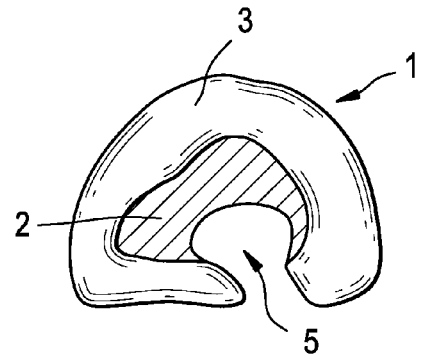
FIG. 3
FIG. 4
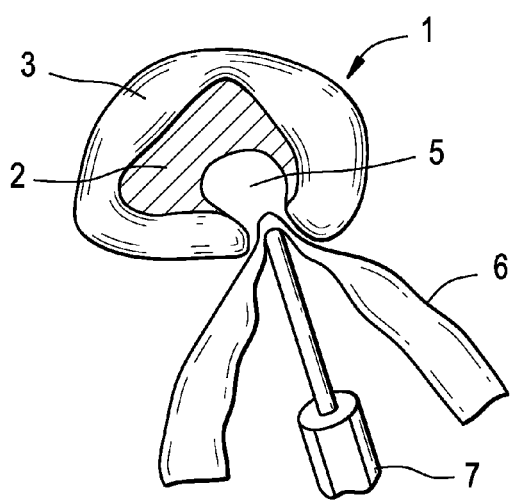
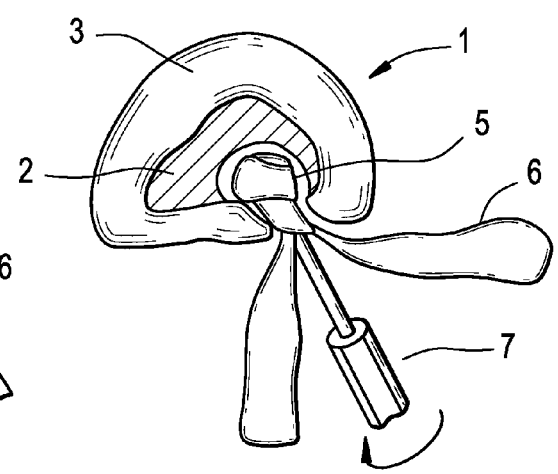
FIG. 5
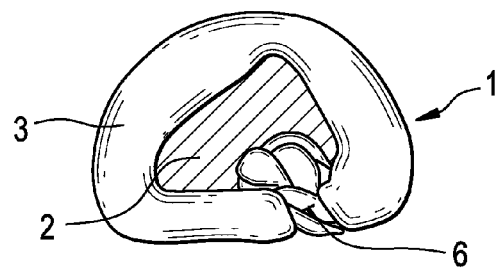

METHOD FOR TREATMENT OF DEFECTS IN THE INTERVERTEBRAL DISC

BACKGROUND OF THE INVENTION

1. Field of the Invention

This invention is concerned with methods for treatment for back pain caused by defects in the intervertebral disc by repairing and/or restoring the nucleus pulposus and intervertebral disc annulus and preventing leakage of the nucleus pulposus.

2. Related Art

Injury and/or degeneration of the intervertebral disc can cause back pain as a result of disc herniation, rupture of the annulus and/or prolapse of the nucleus pulposus. Herniation and nucleus prolapse can cause spinal canal and foraminal stenosis. All may cause release of chemotactic factors that irritate the spinal cord. Acute damage to the annulus and/or nucleus prolapse can cause abnormal biomechanical function of the disc and subsequent disc degeneration.

Discectomy, laminectomy, laminotomy and/or spine fusion procedures represent state of the art surgical treatment for disc problems. Heating the disc using a probe has been suggested to "weld" defects. Injecting curable materials into the nucleus has also been suggested to act as filler material for the nucleus and annular defect.

Lambrecht et. al (PCT/WO00112107A1) disclose a barrier prosthesis such as a plug made of biocompatible material with anchoring means for repairing the annulus and supporting the nucleus pulposus. Disclosed materials include flexible, biocompatible materials, fibrous materials such as collagen or cellulose, and hydrogels. Also disclosed are porous materials that provide tissue ingrowth and bioabsorbable materials, although these are not presented as preferred embodiments.

Ferree (PCT/WO0110316, U.S. Pat. No. 6,245,107) discloses treatment of annular defects using a material which is inserted into the disc in a first insertable state and then is allowed to expand, return or solidify into a second state which occludes the defect. Bioabsorbable materials are mentioned but no disclosure is made regarding materials that are tissue conductive, and no mention is made of SIS. Further, no method is provided whereby a 2-D structure is twisted or packed into the disc structure.

Haldimann (PCT/WO0062832) discloses an in-situ curable polymeric adhesive that is used to fill the disc defect and adhere to the adjacent tissues. Guagliano and Ross (U.S. Pat. No. 6,206,921 B1) disclose a similar system to Haldimann where an injectable, setting, resilient material is used to replace the nucleus pulposus. Stovall (PCT/WO9904720) discloses using a cell containing hydrogel to treat herniated discs. Bao and Yuan (PCT/WO9961084) disclose an expandable, porous material to seal biological apertures and permit tissue ingrowth. Felt et al. (U.S. Pat. No. 6,140,452) disclose an injectable, curable polyurethane to repair tissue sites. Sharkey et al. (U.S. Pat. No. 6,126,682) disclose a method of heating the annulus to weld the defect that can be coupled with a delivery of sealing agents. Gan et al. (U.S. Pat. No. 5,964,807) disclose porous hybrid materials containing sol gel bioactive material that can be used to repair the disc. Plouhar et al. (U.S. Pat. No. 5,922,028) disclose a tissue graft consisting of secured layers of intestinal submucosa which is sculptured to have the anatomical shape of the cartilaginous structure that is to be repaired.

However, the prior art does not disclose any methods whereby a substantially two-dimensionally shaped structure is twisted or packed into the disc structure as hereinafter described and claimed.

BRIEF DESCRIPTION OF THE DRAWINGS

FIG. 1 depicts a cross-sectional view of a spinal disc showing an annular defect with nucleus prolapse.

FIG. 2 shows a cross-sectional view of the spinal disc with a partial neucleotomy.

FIG. 3 depicts a cross-sectional view of the disc of FIG. 2 having a disc repair material being inserted.

FIG. 4 shows the disc of FIG. 3 with further insertion and twisting of the disc defect repair material into the affected disc.

FIG. 5 shows a cross-sectional view of the affected disc with the resulting disc defect material having been inserted.

SUMMARY OF THE INVENTION

Figure 6A:
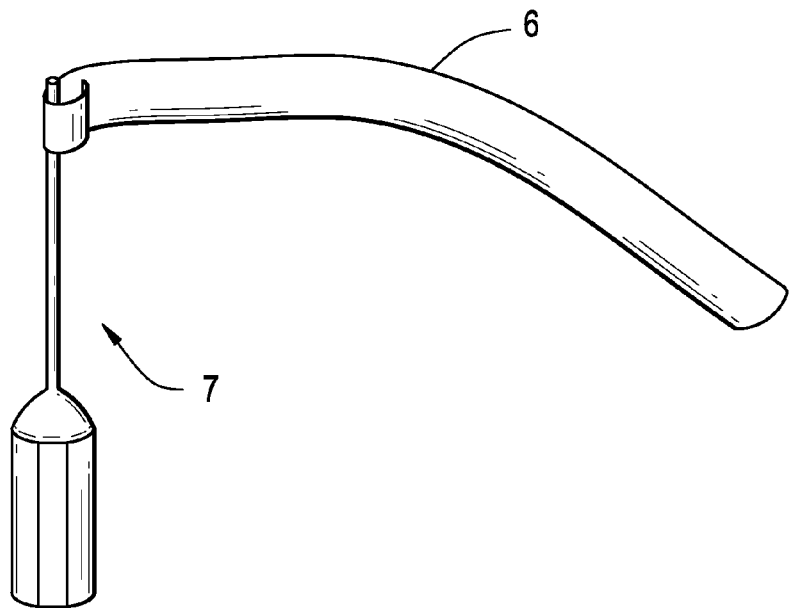
FIGS. 6a, 6b and 6c depict the steps of a second embodiment for the method of this invention.

One embodiment of this invention relates to a method of treating spinal disc defects comprising the steps of:
  a) preparing a disc treatment site;
  b) providing a substantially two-dimensionally shaped disc defect repair material; and
  c) inserting the repair material into the disc to be repaired.

Another embodiment of this invention relates to a method of treating spinal disc defects comprising the steps of:
  a) preparing a disc treatment site;
  b) manipulating a substantially two-dimensionally shaped disc defect repair material into a mushroom shape; and
  c) inserting the repair material into the disc to be repaired.

As hereinafter disclosed and claimed further embodiment of this invention include providing and using the disc defect repair materials that has been seeded with cells and/or treated with bioactive factors.

Advantages of the invention include the fact that it provides a minimally invasive approach to disc repair particularly in maintaining disc height, resisting nucleus leakage and in preferred embodiments promoting regeneration of the native disc structure. The invention has an additional benefit in that the invention permits nucleus pulposus augmentation and annular ring plugging in a single procedure.

DETAILED DESCRIPTION OF PREFERRED EMBODIMENTS OF THE INVENTION

The method of this invention may be more fully understood by reference to the Figures.

FIG. 1 depicts a cross-sectional view of disc 1 comprising nucleus pulposus 2, annular fibrosus or annular ring 3 and a nucleus pulposus prolapse 4 extending through a defect in the annulus fibrosus outside of disc 1.

FIG. 2 describes disc 1 wherein part of nucleus pulposus 2 has been removed creating void 5. It would be noted that, the entire nucleus pulposus 2 may be removed if desired by the surgeon.

FIG. 3 depicts insertion of a substantial two-dimensionally shaped disc defect repair material 6. More particularly, material 6 is inserted with tool 7 into void 5.

FIG. 4 describes further insertion of material 6 with tool 7 into void 5 by use of a clockwise twisting motion.

Finally, FIG. 5 depicts the repaired disc 1 containing material 6 which functions as matrix for both a nucleus pulposus 2 substitute and annulus fibrosis 3 substitute.

Thus the method of this invention in its essential form comprises the steps of:
a) preparing a disc treatment site;
b) providing a substantially two-dimensionally shaped disc defect repair material; and
c) inserting the repair material into the disc to be repaired.

The method also contemplates the step of inserting the repair material in a twisting or turning manner. Such an insertion manner insures penetration into the removed or area devoid of nucleus pulposus portion of the disc. By such a technique, implantation of the material is accomplished by inserting and twisting a strip and facilitating a build-up of material in the disc nucleus and leaving the tail ends to fill the annular defect. (Note FIG. 4)

Additionally, a circular patch of material could be inserted into the nucleus with or without twisting. The ends of the patch may be sutured to the outer annulus to restore circumferential stability to the annulus.

In general, any material extending outside of the annulus may be trimmed away or sutured to the annulus thereby effectively plugging the annulus.

Another embodiment of this invention in its essential form comprises the steps of:
a) preparing a disc treatment site;
b) manipulating a substantially two-dimensionally shaped disc defect repair material into a mushroom shape; and
c) inserting the repair material into the disc to be repaired.

Figure 6B:
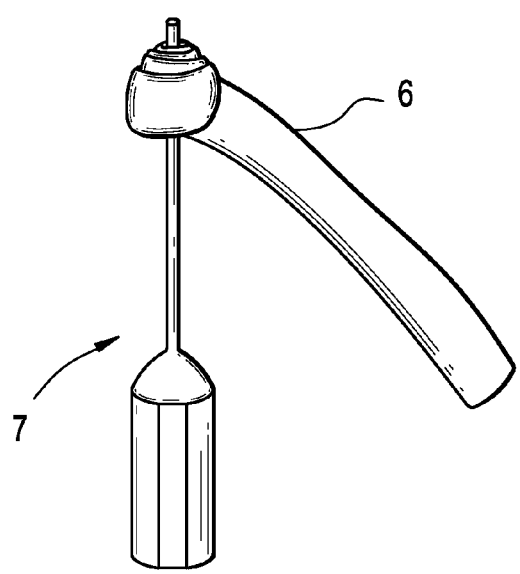
Figure 6C:
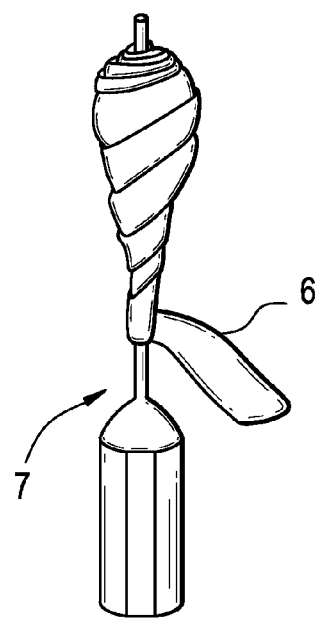

In this embodiment, a two-dimensionally shaped material can be wrapped around an insertion device in such a way as to form a head on the tip of the device as shown in FIGS. 6a-6c while forming a thinner portion below the head. More specifically, FIG. 6a depicts the distal end of tool 7 being wrapped with disc defect repair material 6. As wrapping progresses to FIG. 6b, material 6 at the distal end of tool 7 takes on a mushroom-like shape and when the desired shape and size for material 6 is reached, wrapping of material 6 continues toward the proximal end of tool 7. Desirably, there is a sufficient amount of material 6 to form a tail which serves as a plug for annulus fibrosis 3. Thus, as material 6 is inserted through the annulus 3 into the nucleus pulposus void and the tail occupies the annular defect and serves as a plug. The width of the head is preferably larger than the size of the annular defect. Insertion is possible due to the elastic nature of the annulus. The diameter of the tail region is preferably the same diameter or slightly larger than the annular defect to ensure complete filling.

In some embodiments, the above materials are augmented with an adhesive or sealant material to aid in retention of the plug and prevent herniation around the plug following implantation. Potential materials include platelet-rich plasma clotted with thrombin, fibrin glue, cyanoacrylates, crosslinked proteins (such as gluteraldehyde and albumin) and polymers, and muscle adhesive protein.

The material 6 of the invention is preferably a substantially two-dimensionally shaped structure (e.g., flat), that is the thickness is at least one order of magnitude lower than either the width or length, e.g., of a thickness that will allow folding of the material in a length-wise and/or width-wise manner, such as a strip, or in the case of a flat, circular repair material, where the thickness of the circular material allows the material to fold.

The disc repair material may be selected from a porous, biocompatible material, i.e., a material that is not harmful to and does not cause an undesirable immunological response in a body, e.g., a human being. The biocompatible material may be non-bioabsorbable or bioabsorbable. The porous nature of the defect repair material allows for the material to act as a scaffold for cells to occupy and produce extracellular matrix. Repair cells may migrate from the surroundings following implantation or be seeded onto the repair material prior to implantation. Additionally, bioactive factors may be applied to or incorporated into the disc defect repair material.

Examples of non-bioabsorbable disc defect repair materials include, but are not limited to polyacrylates, ethylene-vinyl acetates (and other acyl-substituted cellulose acetates), polyester (Dacron®), poly(ethylene terephthalate), polypropylene, polyethylene, polyurethanes, polystyrenes, polyvinyl oxides, polyvinyl fluorides, poly(vinyl imidazoles), chlorosulphonated polyolefins, polyethylene oxides, polyvinyl alcohols (PVA), polytetrafluoroethylenes, nylons, and combinations thereof.

The disc repair material of this invention is preferably a porous, bioabsorbable material that is tissue conductive and is desirably, eventually completely replaced by repair tissue. Thus the disc defect repair acts as a temporary support structure for tissue regeneration and resulting in a primarily native repair tissue structure. Preferably the breakdown products of the invention are easily processed by the body through normal metabolic pathways.

Suitable bioabsorbable disc defect repair materials include small intestine submucosa (SIS), collagen, hyaluronic acid, elastin, albumin, reticulin, prolamines, polysaccharides, alginate, heparin, biodegradable polymers of sugar units, synthetic polymers including polylactide, polyglycolide, polydioxanone, polyhydroxybutyrate, polyhydroxyvalerate, poly (propylene fumarate), polyoxaesters, synthetic polyamino acids, biodegradable polyurethanes and their copolymers, and combinations thereof. In one preferred embodiment of this invention, the porous repair material is a textile structure comprised of drawn fibers of the aforementioned materials. In a more preferred embodiment, the fibers are woven or braided into the appropriate scaffold structure mentioned.

A preferred repair material of this invention is small intestinal submucosa (SIS) which is a naturally occurring extracellular collagen based matrix. SIS is described in detail in U.S. Pat. No. 5,372,821, the disclosure of which is hereby incorporated by reference. As described in the '821 patent, SIS is a segment of intestinal tissue of a warm-blooded vertebrate, said segment comprising the tunica submucosa and basilar tissue of the tunica mucosa, said tunica submucosa and basilar tissue being delaminated from the tunica muscularis and the luminal portion of the tunica mucosa of said segment of intestinal tissue. SIS contains cytokines and growth factors and has been shown to act as a resorbable scaffold in vivo that promotes soft tissue regeneration with little scar tissue formation. SIS can be manufactured in laminated sheets of various sizes and thicknesses for different indications. Successful_applications of SIS have included: dural substitution, rotator cuff repair, tendinosis, vessel repair, abdominal and bladder wall repair, and others. However, prior to investigations initiated and directed by the inventors, SIS is not known to have been investigated to determine its ability to facilitate repair or regeneration of disc defects.

While any suitable insertion tool may be used with the method of the invention, a preferred insertion tool has a tip that expands to allow for twisting of the material and retracts so that the tool can be removed.

The invention also contemplates that the disc defect repair material of this invention may be contacted or otherwise cultured with tissue repair cells for a period of time prior to implantation. Alternatively, bioactive factors may be adsorbed onto or absorbed into the repair material prior to implantation.

Examples of suitable repair cells include cells harvested from spinal discs in the body such as nucleus pulposus cells and annulus fibrosis cells. Other examples include but are not limited to: stem cells, bone marrow cells, fibrocytes, adipocytes and chondrocytes.

Additionally, suitable repair cells may be derived from soaking, coating, or otherwise contacting the defect repair material in bone marrow aspirate, platelet rich plasma, platelet poor plasma, whole blood, serum or other autologous media.

Examples of suitable bioactive factors include but are not limited to transforming growth factor-beta and agents in the same family of growth factors, platelet-derived growth factors, fibroblast growth factors, insulin-like growth factors, protein polymers such as RGD-peptides and Indian Hedgehog proteins, anti-inflammatory agents, angiogenic factors, hormones, hyaluronic acid and the like.

More specific examples of suitable transforming growth factor-beta and agents in the same family of growth factors, include, but are not limited to, TGF-$\beta$I, TGF-$\beta$2, and TGF-$\beta$3, GDF-5, MP52, and BMPs (bone morphogenetic proteins).

It should be understood that the foregoing disclosure and description of the present invention are illustrative and explanatory thereof and various changes in the size, shape and materials as well as in the description of the preferred embodiment may be made without departing from the spirit of the invention.

What is claimed is:

1. A method of treating spinal disc defects comprising the steps of
   a) preparing a disc treatment site;
   b) selecting a disc defect repair material comprising small intestinal submucosa (SIS) in the form of a strip having a length, a width, and a thickness, wherein the thickness is at least one order of magnitude lower than either the width or the length; and
   c) inserting the repair material in a twisting manner into the disc treatment site to be repaired to form a mushroom shape.

2. The method of claim 1, wherein the repair material is cell seeded.

3. The method of claim 2, wherein the cells are selected from the group consisting of stem cells, bone marrow cells, fibrocytes, adipocytes, chondrocytes, cells harvested from spinal discs in the body, nucleus pulposus cells, annulus fibrosis cells, and combinations thereof.

4. The method of claim 3, wherein the cells are stem cells.

5. The method of any one of claims 1, and 2-4 wherein the repair material is combined with an autologous medium prior to step c) inserting.

6. The method of claim 5, wherein the autologous medium is selected from the group consisting of platelet-rich plasma, platelet-poor plasma, bone marrow, whole blood and serum.

7. The method of claim 6, wherein the autologous medium is bone marrow.

8. The method of any one of claims 1, and 2-4, wherein the repair material further comprises a bioactive factor.

9. The method of claim 8, wherein the bioactive agent is selected from the group consisting of members of the Transforming Growth Factor-beta (TGF-$\beta$) gene superfamily, platelet-derived growth factors, fibroblast growth factors, insulin-like growth factors, RGD-peptides, Indian Hedgehog proteins, anti-inflammatory agents, angiogenic factors, hormones, hyaluronic acid and combinations thereof.

10. The method of claim 9, wherein the bioactive factor is a Transforming Growth Factor-beta gene superfamily member selected from the group consisting of TGF-$\beta$1, TGF-$\beta$2, TGF-$\beta$3, GDF-5, MP52, and BMPs.

11. The method of claim 5, wherein the repair material further comprises a bioactive factor.

12. The method of claim 11, wherein the bioactive agent is selected from the group consisting of members of the Transforming Growth Factor-beta (TGF-$\beta$) gene superfamily, platelet-derived growth factors, fibroblast growth factors, insulin-like growth factors, RGD-peptides, Indian Hedgehog proteins, anti-inflammatory agents, angiogenic factors, hormones, hyaluronic acid and combinations thereof.

13. The method of claim 12, wherein the bioactive factor is a Transforming Growth Factor-beta gene superfamily member selected from the group consisting of TGF-$\beta$1, TGF-$\beta$2, TGF-$\beta$3, GDF-5, MP52, and BMPs.

14. The method of claim 6, wherein the repair material further comprises a bioactive factor.

15. The method of claim 14, wherein the bioactive agent is selected from the group consisting of members of the Transforming Growth Factor-beta (TGF-$\beta$) gene superfamily, platelet-derived growth factors, fibroblast growth factors, insulin-like growth factors, RGD-peptides, Indian Hedgehog proteins, anti-inflammatory agents, angiogenic factors, hormones, hyaluronic acid and combinations thereof.

16. The method of claim 15, wherein the bioactive factor is a Transforming Growth Factor-beta gene superfamily member selected from the group consisting of TGF-$\beta$1, TGF-$\beta$2, TGF-$\beta$3, GDF-5, MP52, and BMPs.

17. The method of claim 7, wherein the repair material further comprises a bioactive factor.

18. The method of claim 17, wherein the bioactive agent is selected from the group consisting of members of the Transforming Growth Factor-beta (TGF-$\beta$) gene superfamily, platelet-derived growth factors, fibroblast growth factors, insulin-like growth factors, RGD-peptides, Indian Hedgehog proteins, anti-inflammatory agents, angiogenic factors, hormones, hyaluronic acid and combinations thereof.

19. The method of claim 18, wherein the bioactive factor is a Transforming Growth Factor-beta gene superfamily member selected from the group consisting of TGF-$\beta$1, TGF-$\beta$2, TGF-$\beta$3, GDF-5, MP52, and BMPs.

* * * * *